US008260013B2

United States Patent
Pekar et al.

(10) Patent No.: US 8,260,013 B2
(45) Date of Patent: Sep. 4, 2012

(54) DATA REPRESENTATION FOR RTP

(75) Inventors: Vladimir Pekar, Hamburg (DE); Michael Kaus, Hamburg (DE); Ingwer C. Carlsen, Hamburg (DE); Todd R. McNutt, Verona, WI (US); R. Keith Tipton, Verona, WI (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1288 days.

(21) Appl. No.: 11/719,781

(22) PCT Filed: Nov. 4, 2005

(86) PCT No.: PCT/IB2005/053631
§ 371 (c)(1),
(2), (4) Date: May 21, 2007

(87) PCT Pub. No.: WO2006/054194
PCT Pub. Date: May 26, 2006

(65) Prior Publication Data
US 2009/0074264 A1  Mar. 19, 2009

Related U.S. Application Data

(60) Provisional application No. 60/629,913, filed on Nov. 22, 2004.

(51) Int. Cl.
*G06K 9/00* (2006.01)
(52) U.S. Cl. ........ 382/128; 382/131; 382/173; 600/425; 600/426; 378/4; 378/21; 424/9.4; 250/363.04
(58) Field of Classification Search .......... None
See application file for complete search history.

(56) References Cited

U.S. PATENT DOCUMENTS

| | | | | |
|---|---|---|---|---|
| 6,246,783 B1 * | 6/2001 | Avinash | ........ | 382/128 |
| 6,249,594 B1 * | 6/2001 | Hibbard | ........ | 382/128 |
| 6,426,990 B1 * | 7/2002 | Cesmeli | ........ | 378/8 |
| 7,110,003 B2 * | 9/2006 | Doan | ........ | 345/611 |
| 8,165,359 B2 * | 4/2012 | Dewaele et al. | ........ | 382/128 |
| 2001/0033283 A1 * | 10/2001 | Liang et al. | ........ | 345/424 |
| 2003/0002616 A1 * | 1/2003 | Cesmeli | ........ | 378/8 |
| 2003/0208116 A1 * | 11/2003 | Liang et al. | ........ | 600/407 |
| 2003/0233039 A1 * | 12/2003 | Shao et al. | ........ | 600/407 |
| 2004/0013292 A1 * | 1/2004 | Raunig | ........ | 382/128 |
| 2004/0071325 A1 | 4/2004 | Declerck et al. | | |

(Continued)

OTHER PUBLICATIONS

Santos et al., "Multimodality Image Integration for Radiotherpay Treatment, an Easy Approach," 2001 SPIE, pp. 715-723.*

(Continued)

*Primary Examiner* — John Lee

(57) ABSTRACT

An imaging system (10) includes imaging modalities such as a PET imaging system (12) and a CT scanner (14). The CT scanner (14) is used to produce a first image (62) which is used for primary contouring. The PET system (12) is used to provide a second image (56), which provides complementary information about the same or overlapping anatomical region. After first and second images (62, 56) are registered with one another the first and second images (62, 56) are concurrently segmented to outline a keyhole (76). The keyhole portion of the second image (56) is inserted into the keyhole (76) of the first image (62). The user can observe the composite image and deform a boundary (78) of the keyhole (76) by a mouse (52) to better focus on the region of interest within previously defined keyhole.

21 Claims, 4 Drawing Sheets

U.S. PATENT DOCUMENTS

| | | | |
|---|---|---|---|
| 2004/0184647 | A1 | 9/2004 | Reeves et al. |
| 2004/0242987 | A1 | 12/2004 | Liew et al. |
| 2005/0041843 | A1* | 2/2005 | Sawyer ............... 382/128 |
| 2006/0147114 | A1 | 7/2006 | Kaus et al. |
| 2006/0159341 | A1 | 7/2006 | Pekar et al. |
| 2006/0285639 | A1* | 12/2006 | Olivera et al. ........... 378/65 |

OTHER PUBLICATIONS

Rizzo et al., "Integration of CT/PET Images for the Optimization of Radiotherapy Planning," Oct. 25-28, 2001, Proceedings of the 23rd Annual EMBS International conference, pp. 1-3.*

Rizzo et al., "Integration of CT/PET Images For The Optimization of Radiotherapy Planning," Oct. 25-28, 2001, Proceedings of the 23rd Annual EMBS International conference, pp. 1-3.*

Montagnat, J., et al.; Volumetric Medical Images Segmentation using Shape Constrained Deformable Models; http://www.lirmm.fr/manifs/UEE/docs/delingette/pdf/cvrmed.pdf; May 8, 2005.

NSF Engineering Research Center for Subsurface Sensing & Imaging Systems; http://www.censsis.neu.edu/seminars/2004/broysam_051304.pdf; May 8, 2005.

Radiation Oncology Systems: "Multi-Modality Image Fusion";Philips; http://www.medical.philips.com/main/products/ros/products/pinnacle3/features/ Oct. 19, 2004.

Rizzo, G., et al.; Integration of CT/PET Images for the Optimization of Radiotherapy Planning; 2001; Proc. of 23rd Annual EMBS Int'l. Conf.; 2756-2758.

Robb, R. A.; Three-Dimensional Visualization in Medicine and Biology; Handbook of Medical Imaging; 2000; pp. 685-712.

Santos, A., et al.; Multimodality Image Integration for Radiotherapy Treatment, an Easy Approach; 2001; Proc. of SPIE; vol. 4319;pp. 715-723.

Stone, M. C., et al.; The Movable Filter as a User Interface Tool; 1994; Human Factors in Computing Systems Conf. Proc.; pp. 306-312.

"3D Planning"; Philips, Radiation Oncology Systems; May 21, 2007 http://www.medical.philips.com/main/products/ros/products/pinnacle3/3dplanning/.

Bublat, M., et al.; Iterative Multimodal Computer-Assisted Navigation Using Pre- and Intraoperative Image Data; 2002; Med. Laser Appl.; 17:123-131.

Kaus, M. R., et al.; Estimation of Organ Motion from 4D CT for 4D Radiation Therapy Planning of Lung Cancer; 2004; Int'l. Conf. Medical Image Computing and Computer-Assisted Intervention; abstract.

Kim, et al.; Characteristics of a CT/Dual X-Ray Image Registration Method Using 2D Texturemap DRR, Gradient Ascent, and Mutual Information.

McInerney, T., et al.; Deformable Models in Medical Image Analysis: A Survey; 1996; Medical Image Analysis; 1(2) 91-108.

* cited by examiner

DATA REPRESENTATION FOR RTP

CROSS REFERENCE TO RELATED APPLICATIONS

This application claims the benefit of U.S. provisional application Ser. No. 60/629,913 filed Nov. 22, 2004, which is incorporated herein by reference.

The present invention relates to the diagnostic imaging arts. It finds particular application in conjunction with the radiation therapy planning in the oncological studies and will be described with particular reference thereto. However, it is to be appreciated that the present invention is applicable to a wide range of diagnostic imaging modalities and to the study of a variety of organs for a variety of reasons.

In oncological planning, the oncologist typically generates a CT image or a plurality of x-ray, projection images of a region to be treated. The images show bone and other internal structures, but do not necessarily differentiate the tumor from non-cancerous tissue. One of the priorities in oncological procedures is accurately aligning a high power tumor killing x-ray beam with the internal tumor. If the selected trajectory is even slightly off, the x-ray beam will treat most of the tumor, but leave a segment un-irradiated while damaging healthy tissue. Conversely, some tissue is easily damaged by radiation and dense tissue, e.g. bone absorbs a significant portion of the radiation altering the dose. The trajectories are selected to miss these tissues, but often need to come close to them to reach the target. If the trajectory is slightly off, these tissues could be damaged or the dose unknowingly altered.

The radiation beams are adjusted to the shape of the volume to be treated, minimizing radiation to neighboring regions. Each radiation beam is manipulated to reach the patient with different intensity. Making the diameter of the beam too large is detrimental in that it irradiates and harms healthy tissue. Making the beam diameter smaller increases a probability that cancerous tissue goes unirradiated. The more precisely the size, shape, and position of the tumor are known, the narrower the treatment beam can be collimated to minimize the irradiation of surrounding tissue while assuring the irradiation of all cancerous tissue. Accurate target and "organ at risk" delineation is important.

The medical diagnostic images are contoured or segmented to delineate the target anatomical organ such as a bladder or lungs from the surrounding tissue or to delineate the tissues to avoid. Typically, the contouring is carried out in the CT data. CT data allows the definition of the field limits and the contour of the patient region where references, such as fiducial or anatomical markers, are projected. An advantage of the CT data is that it provides information on tissue density, thus allowing calculation of radiation doses. However, CT does not provide sufficient contrast to clearly identify the soft tissue structures in some anatomical locations. For example, in the head-neck area many low-contrast or even invisible structures in the CT data have to be delineated, which is a problematic task. In addition, some patients have allergy to the iodine contrast agents need to obtain information about tumor extension.

The described disadvantages of the CT images can be overcome with the addition of physiological and functional information about the tumor and its surroundings by a use of images from the sources other than the CT dataset. The present application contemplates a new and improved automated registration technique which overcomes the above-referenced problems and others.

In accordance with one aspect of the present invention, a diagnostic imaging system is disclosed. A first scanner obtains a first image of a region of interest of a subject. A second scanner obtains a second image of the region of interest of the subject. A means registers the first and second images with one another such that the first and second images coincide. A means concurrently segments the first and second images to outline a keyhole. A combining means inserts the keyhole portion of the second image in the keyhole of the first image.

In accordance with another aspect of the present invention, a method of diagnostic imaging is disclosed. A first image of a region of interest of a subject is obtained. A second image of the region of interest of the subject is obtained. The first and second images are registered with one another such that the first and second images coincide. The first and second images are concurrently segmented to outline a keyhole. The keyhole portion of the second image is inserted into the keyhole of the first image.

One advantage of the present invention resides in an improved data representation in radiation therapy planning based on complementary information merged with the CT data.

Another advantage resides in an increased efficiency of conventional manual contouring tools.

Another advantage resides in an increased efficiency of automated contouring tools.

Another advantage resides in an improved display which simplifies identification of active tumors.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 3A:
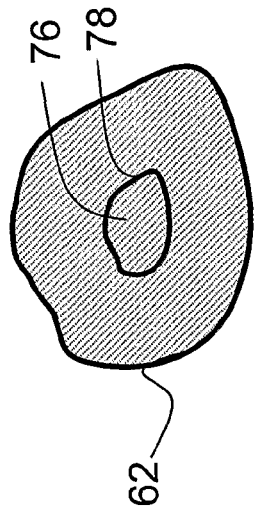
Figure 3B:
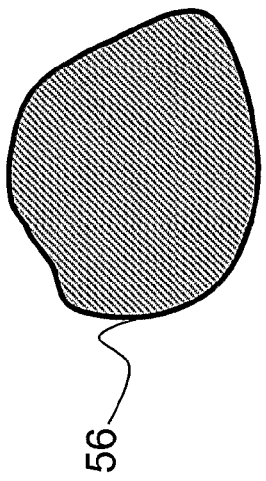
Figure 3C:
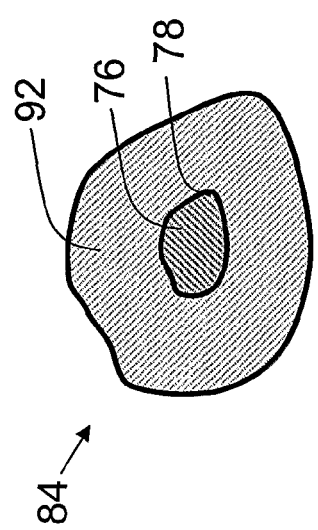

FIGS. 3A and 3B diagrammatically illustrate two images produced by the two modalities;

FIG. 3C diagrammatically illustrates a combined image; and

Figure 4:
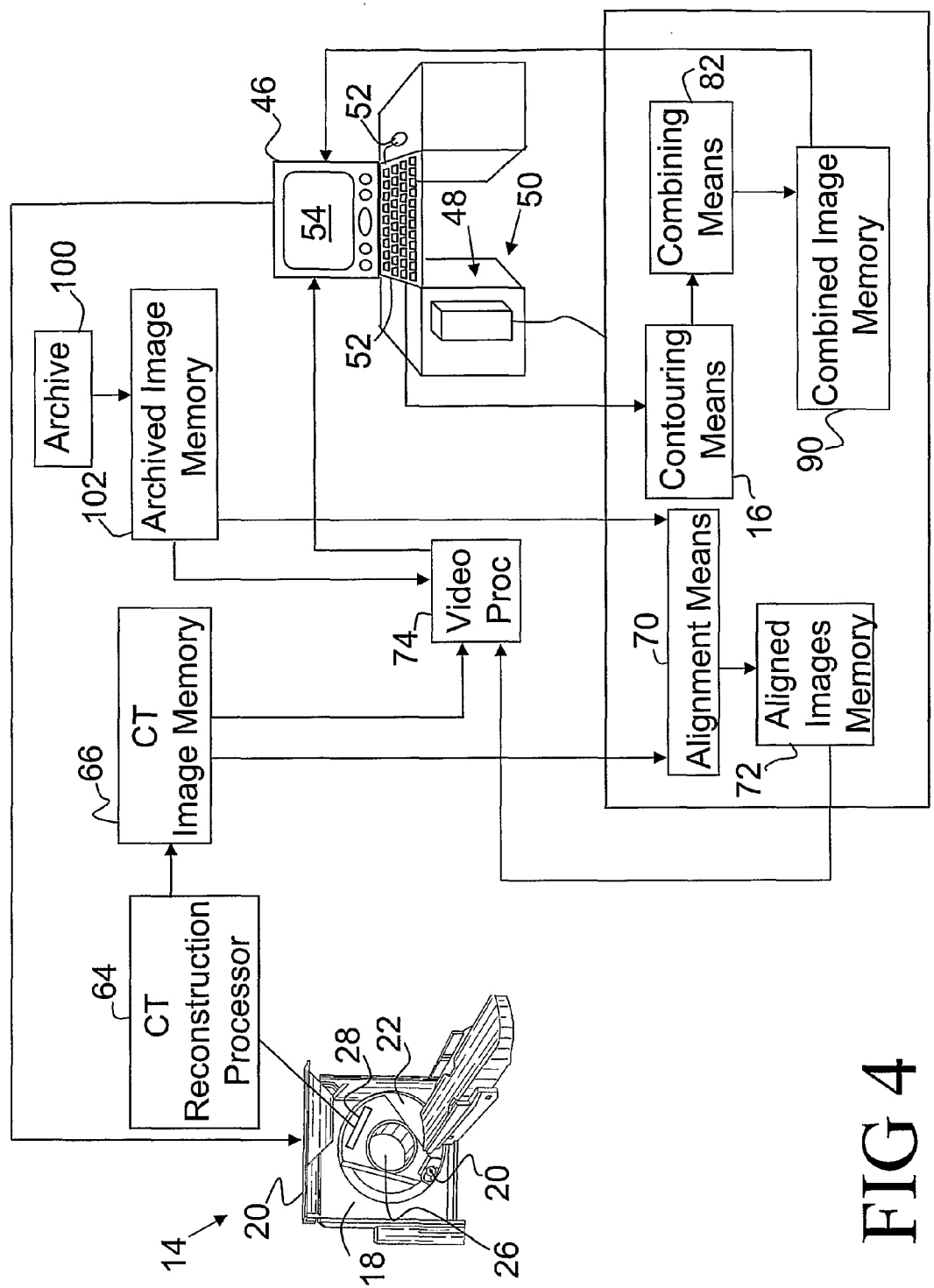

FIG. 4 is a diagrammatic illustration of another imaging system.

Figure 1:
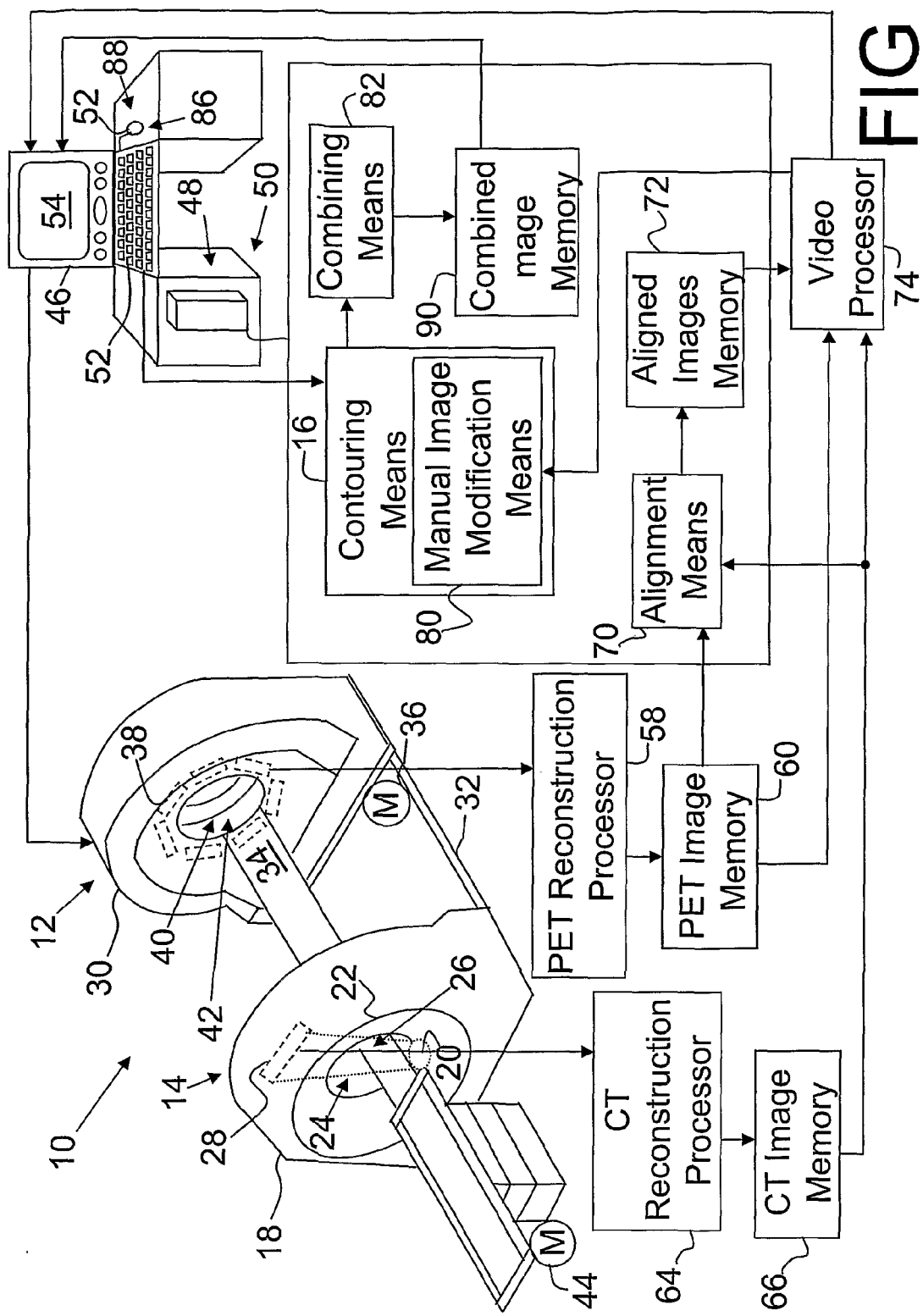
FIG. 1 is a diagrammatic illustration of an imaging system which includes two modalities.

With reference to FIG. 1, a multi-modality system 10 includes complementary modalities, such as a PET imaging system 12, and a computed tomography (CT) scanner 14. The CT scanner 14 is used to produce a primary dataset which is used for contouring by a contouring or segmenting means 16. The complementary modality 12 is used to provide a complementary or secondary dataset which provides complementary information about the same or overlapping anatomical region. The complementary dataset can also be provided by labeled anatomical atlases, other image modalities, e.g. MRI, SPECT, etc., as well as functional images, e.g. fMRI. The complementary data is used to support the automated contouring algorithms by emphasizing other aspects of the image feature space for detecting boundaries of the anatomical structures of interest as well as to increase the efficiency of manual contouring by providing an enhanced viewing environment for the user. For example, in the PET-CT system, the PET creates images of high metabolic activity in the body, rather than creating images of surrounding anatomy. The PET-CT system is particularly helpful in difficult-to-treat regions (e.g. head and neck area, mediastinum, postsurgical abdomen). Typically, before having a PET-CT scan, the subject receives a dose of a radiopharmaceutical. The pharmaceutical concentrates in a particular organ or region and causes radiation to be emitted from this organ or region. During the scan, tracings of the emitted radiation are detected by the PET system creating an image of the distribution of the radiopharmaceutical in the subject. The image can show the circulatory system and/or the relative absorption of the radiopharmaceutical in various regions or organs. Integration of the anatomical data from the CT scan with the metabolic data from the PET scan in the PET-CT image gives physicians additional visual information to determine if disease is present, the location and extent of disease, and establish an appropriate treatment plan.

With continuing reference to FIG. 1, the CT scanner 14 includes a non-rotating gantry 18. An x-ray tube 20 is mounted to a rotating gantry 22. A bore 24 defines an examination region 26 of the CT scanner 14. An array of radiation detectors 28 is disposed on the rotating gantry 22 to receive radiation from the x-ray tube 20 after the x-rays transverse the examination region 26. Alternatively, the array of detectors 28 may be positioned on the non-rotating gantry 18.

Figure 2:
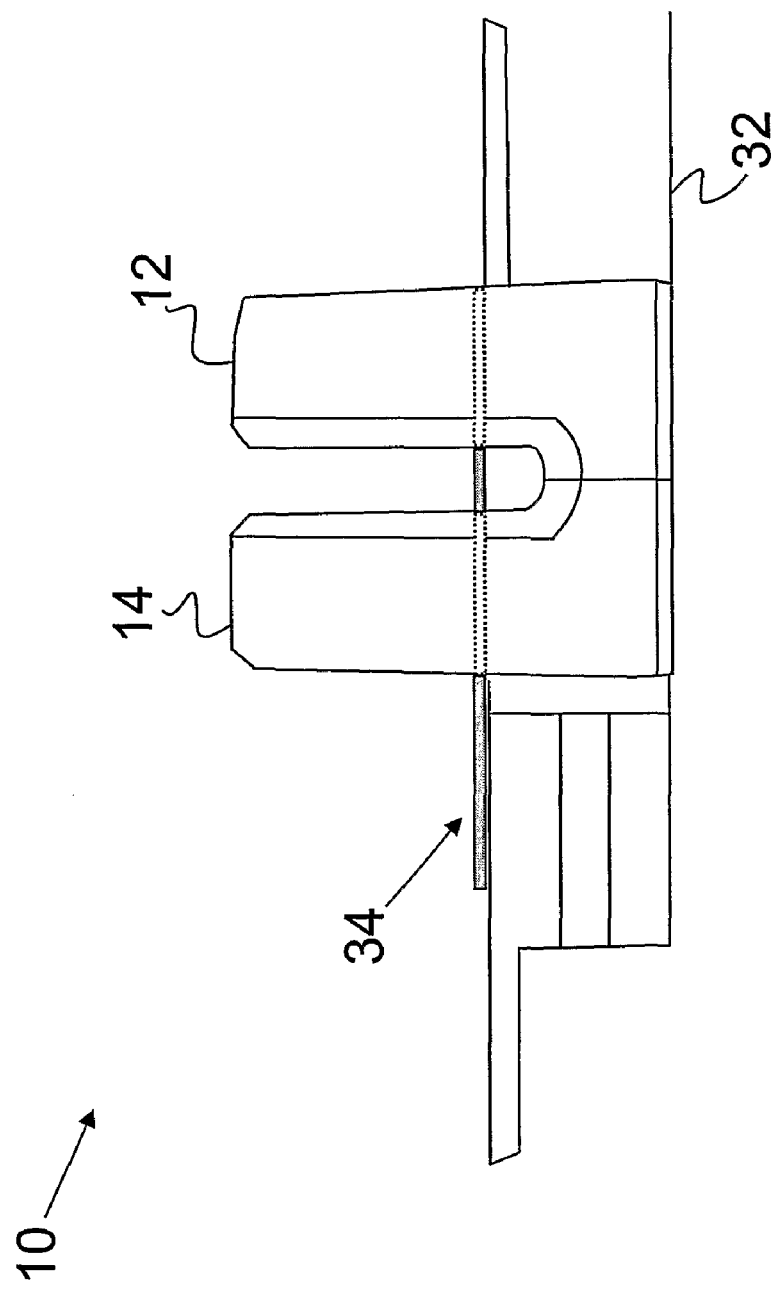
FIG. 2 is a diagrammatic illustration of the two modalities forming a closed system.

The PET imaging system 12 includes a positron emission tomography (PET) scanner 30 which is mounted on tracks 32. The tracks 32 extend in parallel to a longitudinal axis of a subject support or couch 34, thus enabling the CT scanner 14 and the PET scanner 30 to form a closed system as seen in FIG. 2. A moving means 36, such as a motor and a drive, is provided to move the scanner 30 in and out of the closed position. Detectors 38 are preferably arranged in a stationary ring around a bore 40 which defines an examination region 42. The rotatable detector heads are also contemplated. A couch moving means 44, such as a motor and a drive, provides a longitudinal movement and vertical adjustment of the couch 34 in the examination regions 26, 42.

With continuing reference to FIG. 1 and further reference to FIGS. 3A and 3B, an imaging technician performs a scan using a workstation 46 which includes a CPU processor or hardware means 48 and a software means 50 for carrying out the image processing functions and operations. The workstation 46 preferably includes one or more input devices 52 (e.g., a computer keyboard, mouse, etc.), and one or more monitors or displays 54. The user, via the input devices 52, can selectively control the workstation 46 and/or the entire system 10. The couch 34, which carries a subject, is moved by the couch moving means 44 into the examination region 42 for a complementary or PET image 56 to be generated by the PET scanner 30. Electronic data is reconstructed into a PET image by a PET reconstruction processor 58 and stored in a PET image memory 60. The couch moving means 44 moves the couch 34 to position the couch carrying the subject in the CT scanner examination region 26, where a primary or CT image 62 is taken. More particularly, the couch 34 with the subject is moved to the position in the CT examination 26 region that is geometrically and mechanically predicted as being the same as its imaged position in the PET imaging region 42. Electronic data is reconstructed into a 3D CT image by a CT reconstruction processor 64 and stored in a CT image memory 66.

The complementary and CT images 56, 62 are aligned or registered with one another by an image alignment processor or means 70 such that common reference; points in the complementary and CT images 56, 62 coincide. More specifically, the alignment processor 70 carries out relative scaling, translations and/or rotations of the images to compensate for the subject movement between the scanners 30, 14 and applies additional scaling, translation, rotation and other linear and non-linear transforms in order to attain registration of the common reference points in both images. The references points are preferably readily identifiable, such as well defined anatomical landmarks, which experience little to no movement or relative displacement with respect to one another from the complementary image 56 to the CT image 62. For example, the reference points may be the tips of bones which are substantially stationary in view of, or relative to, the movement experienced by the tissue mass under consideration. Optionally, fiducials or other like artificial landmarks, which can be visualized in the images, are applied during imaging and used as the reference points for alignment purposes.

In one embodiment, the alignment processor 70 automatically registers the images 56, 62 in response to the user's selection of the reference points in each image. Alternately, the alignment processor 70 enables manual registration or registration adjustment by the user. In either case, the alignment may take place after the images have been marked, or prior to the marking. The aligned images are stored in an aligned images memory 72. To provide human-viewable depictions (e.g., 3D representations, 2D cross-sections, surface rendering, etc.) of the aligned images 56, 62, the image data in the aligned images memory 72 is appropriately formatted by a video processor 74 for display on the monitor 54. Preferably, the PET and CT images 56, 62 are presented in a side-by-side relationship on the display 54. Alternatively, the images 56, 62 are presented in an overlaid fashion. The user uses the input means 52 to control display of the images 56, 62.

With continuing reference to FIGS. 1, 3A and 3B, and further reference to FIG. 3C, the contouring means 16 segments the CT image 62 to delineate a keyhole 76, e.g. to specify a specific anatomical target volume with a target boundary 78, such as an organ of interest. The target boundary 78 is adjusted by the user by a use of a manual image modification means 80. The manual image modification means 80 includes manual local tools which allow the user to manipulate local regions of the interface in the CT image 62 to set up the target boundary 78 with the use of the input means 52. For example, a manual tool such as a pencil might be used to deform or draw the boundary 78, a series of blunt and shape-deforming tools or the like. Although the operator typically contours or segments on the CT image, the same contour or segment is concurrently defined in the PET image. Of course, adjusting the contour or segment in the PET image makes the same change in the CT image.

A combining means 82 replaces the contoured or segmented portion, i.e. the contoured keyhole 76 in the CT image with the corresponding portion of the PET image. In this manner, the region of interest in the PET scan is surrounded by a CT image which provides easier to read anatomical information to assist in locating the region of interest relative to the subject. Alternately, the inserted region of interest can be enhanced by combining or superimposing it with images from another modality or other enhancement techniques. The image combination and/or superimposing techniques and other algorithms, as are known in the art, are employed by the combining means 82. In this manner, a combined image 84 preferably visualizes both: (i) the precise size and shape of and metabolic information about the tissue mass or a target organ under consideration (i.e., from the complementary image 56); and, (ii) an accurate map of the surrounding tissue including the relative location of risk tissue which could be damaged by the treatment beam (i.e., from the CT image 62). With continuing use of the manual image modification means 80, the user can move the boundary 78 by the mouse 52, for example, to better focus on the region of interest within previously defined keyhole. In this manner, the operator can use the metabolic information to fit the keyhole more accurately to target tissue within the target organ. In one embodiment, the user can use a left button 86 of the mouse 52 to pull the CT image 62 and a right button 88 of the mouse 52 to pull the PET image 56. In this manner, the user can flip back and forth between the PET image 56 and the CT image 62 in the keyhole.

In one embodiment, the combining means 82 superimposes a fused image from two or more different modalities over the keyhole 76. The fusion of images from different modalities is known in the art. Superimposing a fused image over the keyhole 76 is particularly advantageous in one embodiment where an autosegmentation process is used, since the autosegmentation of the CT data can be difficult due to the insufficient contrast of some soft tissues. The autosegmentation typically uses a 3D predetermined model of the region of interest in the diagnostic image. Thus, in one embodiment, the autosegmentation can be started with the selected model and further accurately manually completed with superimposing a fused image of multiple modalities over the keyhole 76 and manually adjusting the boundary 78.

The 3D combined or superimposed image 84 from the combining means 82 is stored in a combined image memory 90 (or like electronic, magnetic, optical, or other storage device) where it may be selectively accessed by the workstation 46. Preferably, the image memory 90 is incorporated in the workstation 46.

In one embodiment, the workstation 46 is set up for treatment planning. More specifically, the combining means 82 superimposes a planning image over the combined image 84, including the keyhole 76. This allows a better definition of a tumor mass defining optimized volumes of interest for radiotherapy to more precisely design the radiation beams' geometry. Treatments such as radiotherapy are simulated on the hardware 48 with the results being displayed on the monitor 54.

For example, in one simulation, various doses of radiation are scheduled for delivery to selected regions in the combined image 84. The simulation allows the user to plan the treatment and review simulated results prior to actual implementation on the subject. A first dose may be scheduled for a first trajectory through the region or volume corresponding to the target tissue in the keyhole 76, e.g. a tumor. The target tissue may be smaller than the keyhole 76 or the keyhole 76 can be sized to match the target tissue. Consequently, the first dose delivery is accurately simulated in the planning, and can be accurately performed on the subject. Likewise, a second dose may be scheduled for a second trajectory through the region or volume corresponding the target tissue. This process is repeated along the plurality of trajectories to be sure all beams squarely intersect the target tissue and avoid risk tissue.

With reference to FIG. 4, a patient who is undergoing treatment for lung cancer, for one example, is positioned in the CT scanner 14 for a follow-up examination to have the lungs re-inspected. The oncologist compares the current images from the CT scanner stored in the CT image memory 66 with the images of the patient that were taken at an earlier time. Based on this comparison, the oncologist can determine the rate of progression of the disease, the progress of the treatment, whether it is in remission, and correspondingly adjust the radiotherapy treatment.

Image data from the hospital archive or from another storage medium 100 of the keyhole region of the same patient is retrieved and stored in an archived 3D volumetric image memory 102. Of course, both the CT image and archive image memories 66, 102 may be parts of a common storage medium. The alignment means 70 retrieves the current and archived images and automatically registers the two images for a concurrent display on the monitor 54. When the alignment processor 70 discovers the discrepancies in the current and archived images, the contouring means 16 automatically positions the keyhole 76 over the areas with major distortions. The user is so guided to recheck the image in the keyhole 76 to determine whether the change is caused by the actual change in the tumor in response to the therapy or by the patient's motion. The therapist then can assess and/or revise the treatment plan.

In another embodiment, the keyhole 76 displays a series of temporally changing images. For example, if images were generated at a plurality of preceding treatment sessions, all of the preceding images are contoured to define the same keyhole. The keyhole 76 surrounded by the current image serially displays the corresponding regions of the preceding images in temporal order. As another example, the keyhole 76 displays the evolution of a PET or SPECT image over time as the radiopharmaceutical is absorbed or washes out.

In other embodiments, two or more keyholes 76 are defined. Each keyhole 76 could define a different tumor or some could define tumors and others risk tissue. Although described with reference to CT and PET images, other combinations of diagnostic imaging techniques (ultrasound, MRI, SPECT, fluoroscopy, digital x-ray, and the like) are also contemplated.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging system comprising:
    a first scanner which obtains a first image of a region of interest of a subject;
    a second scanner which obtains a second image of the region of interest of the subject;
    a registering processor which registers the first image and the second image with one another such that the first image and second image coincide;
    a segmentation processor which concurrently segments the registered first image and the registered second image to outline a corresponding keyhole portion with a first boundary in the first registered image and a second boundary in the second registered image, the first and second boundaries being spatially the same such that modifying the first boundary modifies the second boundary spatially correspondingly and modifying the second boundary modifies the first boundary spatially correspondingly; and
    a combining processor which inserts the keyhole portion of the registered second image in the keyhole portion of the registered first image.

2. The system as set forth in claim 1, wherein the first scanner and the second scanner generate diagnostic images with a different modality.

3. The system as set forth in claim 2, wherein the modalities include at least two of PET, SPECT, MRI, ultrasound, fluoroscopy, CT, and digital x-ray.

4. The system as set forth in claim 1, wherein the combining processor fuses the keyhole portion of the second image with the keyhole portion of the first image.

5. The system as set forth in claim 1, wherein the segmenting processor includes:
   a user interface for manually modifying the first and second boundaries concurrently of the first and second keyholes.

6. The system as set forth in claim 1, wherein the first scanner generates the first image and stores the first image in a first memory and wherein the second image was generated at an earlier time and further including:
   an archive, from which the second image is withdrawn and loaded into a second memory, and the registering processor automatically triggers the segmentation processor to select an area of a major distortion between the first image and the second image as the keyholes portions.

7. The system as set forth in claim 1, wherein the first scanner generates the first image and the second scanner generates a series of second images depicting evolution and treatment of a tumor over time and further including:
   an archive, from which the keyhole portions of the series of second images are withdrawn and loaded into a second memory; and
   wherein the combining processor inserts the second image keyhole portions in the keyhole of the first image in a temporal order.

8. The system as set forth in claim 1, wherein the combining processor superimposes a planning image of the subject and further including:
   a radiation therapy planning workstation which is used by a user to simulate a radiation therapy treatment session.

9. The system as set forth in claim 1, wherein the first scanner and the second scanner are correspondingly a CT scanner and a PET scanner.

10. A method of diagnostic imaging comprising:
    obtaining a first image of a region of interest of a subject;
    obtaining a second image of the region of interest of the subject;
    registering the first image and the second image with one another such that the first image and the second image coincide;
    concurrently segmenting the first image and the second image to outline a keyhole in the first image with a first boundary and a spatially corresponding keyhole portion of the second image with a second boundary;
    concurrently modifying the first and second boundaries such that the first and second boundaries remain spatially corresponding; and
    inserting the keyhole portion of the second image into the keyhole of the first image.

11. The method as set forth in claim 10, wherein the first image and the second image are generated with a different modality.

12. The method as set forth in claim 11, wherein the modalities include at least two of PET, SPECT, MM, ultrasound, fluoroscopy, CT, and digital x-ray.

13. The method as set forth in claim 10, wherein the step of inserting includes:
    fusing the keyhole portion of the second image with a portion of the first image disposed in the keyhole.

14. The method as set forth in claim 10, wherein the step of segmenting includes:
    manually modifying the first and second boundaries of the first and second keyholes.

15. The method as set forth in claim 10, wherein the second image was previously generated and stored in an archive and further including:
    generating the first image of the region of interest of the subject;
    obtaining the second, previously generated image from the archive ; and
    automatically selecting an area of a major difference between the first image and the second image as the keyhole.

16. The method as set forth in claim 10, wherein the second image is one of a series of second images which depict treatment and evolution of a tumor over time and wherein the segmenting step includes segmenting the tumor to define the keyhole and the keyhole portion and further including:
    inserting the keyhole portion of each of the series of second images in the keyhole of the first image in a temporal order.

17. The method as set forth in claim 10, wherein the step of inserting includes superimposing a planning image of the subject and further including:
    simulating a radiation therapy treatment session at a radiation therapy workstation.

18. The method as set forth in claim 10, wherein the first image is generated with a CT scanner and the step of obtaining the second image includes:
    generating the second image with a PET scanner.

19. The method as set forth in claim 10, further including:
    toggling the keyhole portions of the second image in the keyhole of the first image.

20. An imaging apparatus for performing the method of claim 10.

21. A diagnostic imaging system comprising:
    a first scanner for obtaining a first image of a region of interest of a subject;
    a second scanner for obtaining a second image of the region of interest of the subject;
    a user input device; and
    a processor programmed to perform the steps of:
        registering the first image and the second image with one another such that the first image and the second image coincide;
        concurrently segmenting the first image and the second image to outline a spatially corresponding keyhole in the first and second images with first and second spatially corresponding outlines;
        with the user input device, concurrently modifying the first and second outlines, such that the first and second outlines remain spatially corresponding; and
        inserting a keyhole portion of the second image defined by the second outline in the keyhole of the second image into the keyhole of the first image defined by the first outline.

* * * * *